US012642608B2

(12) United States Patent     (10) Patent No.:   US 12,642,608 B2

Shang et al.     (45) Date of Patent:     Jun. 2, 2026

(54) TENSIONING RIG AND METHOD

(71) Applicant: Precision Robotics Limited, London (GB)

(72) Inventors: Jianzhong Shang, Dartford (GB); Tamas Csaba Hernadi, London (GB); Etienne Francois Joseph Dondez, Dijon (FR)

(73) Assignee: Precision Robotics Limited, London (GB)

( * ) Notice: Subject to any disclaimer, the term of this patent is extended or adjusted under 35 U.S.C. 154(b) by 288 days.

(21) Appl. No.: 18/277,167

(22) PCT Filed: Feb. 9, 2022

(86) PCT No.: PCT/GB2022/050348
§ 371 (c)(1),
(2) Date: Aug. 14, 2023

(87) PCT Pub. No.: WO2022/172004
PCT Pub. Date: Aug. 18, 2022

(65) Prior Publication Data
US 2024/0115330 A1     Apr. 11, 2024

(30) Foreign Application Priority Data

Feb. 12, 2021    (GB) ..................................... 2101984

(51) Int. Cl.
*A61B 34/30*     (2016.01)
*B25B 27/14*     (2006.01)
*A61B 34/00*     (2016.01)

(52) U.S. Cl.
CPC ............ *A61B 34/30* (2016.02); *B25B 27/146* (2013.01); *A61B 2034/715* (2016.02)

(58) Field of Classification Search
CPC .... A61B 2017/00526; A61B 2034/715; A61B 34/30; A61B 34/71; B25B 27/146
See application file for complete search history.

(56) References Cited

U.S. PATENT DOCUMENTS

| | | | |
|---|---|---|---|
| 4,971,075 A | 11/1990 | Lee | |
| 7,137,617 B2 | 11/2006 | Sjostedt | |
| (Continued) | | | |

FOREIGN PATENT DOCUMENTS

| | | |
|---|---|---|
| CN | 112754545 A | 5/2021 |
| EP | 1036914 A1 | 9/2000 |
| (Continued) | | |

OTHER PUBLICATIONS

International Search Report from PCT International Application No. PCT/GBGB2022/050348 dated May 13, 2022.
(Continued)

*Primary Examiner* — Scott Luan
(74) *Attorney, Agent, or Firm* — Budzyn IP Law, LLC

(57) ABSTRACT

A tensioning rig for tensioning a plurality of tendons comprising: a plurality of weights; a plurality of primary pulleys spaced apart from one another along a first axis; a plurality of secondary pulleys spaced apart from one another; and a plurality of tensioning wires, each engageable with a respective primary and secondary pulley, and comprising a first end comprising a tendon portion and an opposite end comprising a weight portion, wherein the tendon portion is removably attachable to a respective tendon and extendable from the respective tendon to the respective primary pulley substantially along the first axis and the weight portion is attachable to a respective weight and extendable from the respective secondary pulley to the respective weight, each (Continued)

tensioning wire further comprising an intermediate portion extending from the respective primary pulley to the respective secondary pulley.

9 Claims, 5 Drawing Sheets

(56)                    References Cited

U.S. PATENT DOCUMENTS

| | | | |
|---|---|---|---|
| 2003/0010966 A1* | 1/2003 | Sjostedt | ................... B32B 1/08 |
| | | | 254/231 |
| 2010/0082041 A1 | 4/2010 | Prisco | |
| 2011/0146441 A1 | 6/2011 | Graham et al. | |
| 2011/0287403 A1 | 11/2011 | Ciccone, II et al. | |
| 2014/0128849 A1 | 5/2014 | Au et al. | |
| 2019/0046173 A1 | 2/2019 | Cooper et al. | |
| 2019/0200969 A1* | 7/2019 | Stanton | .................. A61B 17/00 |
| 2020/0121169 A9 | 4/2020 | Lund et al. | |

FOREIGN PATENT DOCUMENTS

| | | | |
|---|---|---|---|
| GB | 2586998 A | 3/2021 | |
| WO | 9950527 A | 10/1999 | |

OTHER PUBLICATIONS

Search Report from Great Britain Application No. GB2101984.9 dated Jul. 14, 2021.

* cited by examiner

TENSIONING RIG AND METHOD

CROSS-REFERENCE TO RELATED APPLICATIONS

This application is a National Stage Application under 35 U.S.C. § 371 of PCT Application No. PCT/GB2022/050348, filed Feb. 9, 2022 which claims priority to UK Patent Application No. GB2101984.9, filed Feb. 12, 2021, the entire contents of which are incorporated by reference herein.

BACKGROUND OF THE INVENTION

1. Field of the Invention

This invention relates to a tensioning rig for tensioning a plurality of tendons and to a method of crimping a plurality of tendons. The invention has particular, although not exclusive, application in the field of manufacturing, maintaining and/or repairing tendon driven surgical robotic instruments. The invention may also be applied to tendon driven robotics outside of the surgical field or other types of tendon driven instruments.

From herein the invention is primarily described in relation to application in the field of surgical robotics. However, this is for demonstrative purposes only and is not to the exclusion of the invention's application in other fields.

2. Description of the Related Art

Known surgical robotic instruments comprise a drive module, a shaft extending from the drive module, an articulation portion coupled to the shaft and an end effector coupled to the articulation portion. The drive module may comprise a plurality of actuators that are driven by motors to which the driver module is couplable. Each actuator may be attached to a tendon that extends from the driver module, through the shaft, to the articulation portion or end effector where they may be attached to a rotatable joint, for example. The articulation portion and end effector may therefore be actuated by controlling the actuators in the driver module to pull different tendons. In other words, the actuation portion and end effector are tendon driven.

The drive modules of some known surgical robotic instruments comprise capstan actuators which may be attached to a tendon and then rotated to wrap the tendon about the capstan and tension the tendon as required. However, such actuators are expensive to manufacture at the small scale required for minimally invasive surgical instruments and may require complex and precise methods for coupling the actuators to the motors which drive them when the surgical instrument is in use.

Some known surgical robotic instruments comprise drive modules with linearly moving actuators which may be manufactured more cost effectively at the scales required, particularly as the drive module may preferably be disposable, single-use parts to ensure sterility for use in surgical procedures. However, repeatably and accurately tensioning tendons attached to linear actuators can be more difficult than tensioning tendons attached to capstan actuators, particularly as the tendons should ideally be tensioned so that they extend substantially parallel to one another and in close proximity to one another as they do when in use.

SUMMARY OF THE INVENTION

According to a first aspect of the invention, there is provided a tensioning rig for tensioning a plurality of tendons comprising: a plurality of weights; a plurality of primary pulleys spaced apart from one another along a first axis; a plurality of secondary pulleys spaced apart from one another; and a plurality of tensioning wires, each engageable with a respective primary and secondary pulley, and comprising a first end comprising a tendon portion and an opposite end comprising a weight portion, wherein the tendon portion is removably attachable to a respective tendon and extendable from the respective tendon to the respective primary pulley substantially along the first axis and the weight portion is attachable to a respective weight and extendable from the respective secondary pulley to the respective weight, each tensioning wire further comprising an intermediate portion extending from the respective primary pulley to the respective secondary pulley.

The plurality of tendons may form part of a tendon driven instrument such as a tendon driven surgical robotic instrument wherein each tendon comprises a first end attached to a component of the instrument to be drivable via actuation of the tendon, such as a rotatable joint, and a second end.

By means of the first aspect of the invention, each tendon may be tensioned by attaching the opposite end of each tendon to the tendon portion of a respective tensioning wire and attaching a respective weight from the weight portion of the tensioning wire. Each tendon may therefore be tensioned to a predetermined degree dependent on the weight that is used. The plurality of tendons may be tensioned equally, or one or more tendons may be tensioned to a different degree to other tendons. Further, the amount of tensioning is accurately repeatable across a plurality of tendon driven instruments.

In use, each tensioning wire is engaged with a respective primary pulley. The primary pulleys are spaced apart from one another along the first axis and, in use, the tendon driven instrument may be positioned, by a user, substantially in alignment with the first axis such that the tendon portion of each tensioning wire and each tendon extends substantially along the first axis. In use, the user would ideally position the tendon driven instrument so that it is sufficiently aligned with the first axis for the tendon portion of each tensioning wire and each tendon to extend less than 10° from the first axis. More preferably, the tendon portion of each tensioning wire and each tendon would extend less than 5° from the first axis or, even more preferably, less than 1° from the first axis.

The positioning of the primary pulleys may therefore facilitate tensioning of each of the tendons simultaneously while they extend substantially parallel to one another and in close proximity to one another. This may advantageously allow the plurality of tendons to be attached to actuators in the tendon drive instrument whilst being positioned as they would be when the tendon drive instrument is in use. For example, the tensioning rig may be suitable to tension a plurality of tendons to enable crimping of each of the plurality of tendons within a respective ferrule forming part of an actuator in a tendon driven instrument.

Each tensioning wire is also engaged with a respective secondary pulley wherein the respective weight may hang below the secondary pulley via the tensioning wire, particularly the weight portion of the tensioning wire which is extending from the respective secondary pulley to the respective weight. Each of the plurality of secondary pulleys are spaced apart from one another, thereby providing space for the weights to be spaced apart from one another and avoid one weight resting on or supporting another weight.

The plurality of secondary pulleys may be positioned in any suitable position relative to the plurality of primary pulleys allowing the intermediate portion of each tensioning wire to extend from the respective primary pulley to the respective secondary pulley. For example, the secondary pulleys may be spaced apart from the first axis as their positioning has no effect on the alignment of the tendons relative to the first axis. This may facilitate the secondary pulleys being able to be spaced apart sufficiently for the weights hanging below them to also be spaced apart. It may also facilitate the secondary pulleys to be positioned so that the tensioning rig has a compact footprint and may be portable and/or readily mounted to a worktop. For example, the secondary pulleys may be positioned in a plurality of rows rather than in one continuous line substantially along the first axis.

In embodiments of the invention the tensioning rig may further comprise a plurality of first auxiliary pulleys, each of which first auxiliary pulleys is positionable between a respective primary and secondary pulley and is engageable with the tensioning wire.

In such embodiments of the invention, each first auxiliary pulley may be positioned to improve the route that the respective tensioning wire takes as it extends from the respective tendon to the respective weight. For example, each first auxiliary pulley may be positioned to improve the angles at which the tensioning wire engages with the primary and/or secondary pulley, facilitate a neater and/or more compact configuration of tensioning wires and/or facilitate greater spacing apart of the secondary pulleys relative to the spacing of the primary pulleys.

In embodiments of the invention the tensioning rig may further comprise a plurality of second auxiliary pulleys, each of which second auxiliary pulleys is positionable between respective primary and secondary pulleys and is engageable with the tensioning wire.

In such embodiments of the invention, each second auxiliary pulley may be positioned to improve the route that the respective tensioning wire takes as it extends from the respective tendon to the respective weight, similarly to each first auxiliary pulley.

Further, the tensioning rig may comprise any suitable number of auxiliary pulleys to facilitate the required routing of the tensioning wires to improve engagement with the primary and or secondary pulleys, neatness and/or compactness of the tensioning rig and/or spacing of the secondary pulleys, for example.

In embodiments of the invention, the tensioning rig may further comprise a base on which the plurality of primary pulleys are supported, and a support extending from the base and adapted to support the plurality of secondary pulleys above the base.

In such embodiments of the invention, the support may be adapted to provide sufficient space beneath the secondary pulleys for the respective weights to hang freely below them.

The base may be a floor, a static worktop or a moveable platform mountable to other surfaces thereby enabling the tensioning rig to be portable.

In embodiments of the invention, each tensioning wire is removably attachable to a respective weight.

In such embodiments the weights may be variable and interchangeable to facilitate a range of different tensions to be applied to each tendon via the tensioning wires. The tensioning wires may also be readily interchangeable so that each tensioning wire may be replaced easily if it is damaged or worn, for example.

In embodiments of the invention, one or more weights of the plurality of weights may have an equal weight or a different weight to other weights.

In such embodiments of the invention, one or more tendons of the plurality of tendons may be tensioned equally or to a different degree to other tendons, according to the weight which is attached to the respective tensioning wire or wires.

According to a second aspect of the invention, there is provided a method of crimping a plurality of tendons within a respective plurality of ferrules wherein each tendon comprises a first end and second end, the method comprising the steps of threading each of the plurality of tendons through a respective one of the plurality of ferrules, fixing the first end of each tendon such that it is immobilised relative to its respective ferrule, attaching the second end of each tendon to a first end of a respective one of a plurality of tensioning wires, hanging one of a plurality of predetermined weights from a second end of each tensioning wire, thereby tensioning each tendon, and crimping each ferrule to its respective tendon.

The plurality of tendons may form part of a tendon driven instrument such as a tendon driven surgical robotic instrument. The first end of each tendon may be attached to a component of the instrument to be drivable via actuation of the tendon, such as a rotatable joint, and the step of fixing the first end of each tendon may comprise immobilising the component to which it is attached.

Each ferule may form part of a respective linearly moveable actuator. The step of fixing the first end of the tendon such that it is immobilised relative to its respective ferrule may further comprise immobilising the ferrules.

By means of the second aspect of the invention, each of a plurality of tendons may be crimped to its respective ferrule while under a predetermined degree of tension dependent on the weights used. The weights may be determined to provide sufficient tension in the tendons to ensure that there is no slack in the instrument whilst at the same time ensuring that the instrument isn't too stiff to actuate effectively, and that the degree of tension is not too close to the tendon's tensile strength.

Further, the method is repeatable so that a plurality of tendon driven instruments may be reliably manufactured and/or repaired such that tendons are under the correct amount of tension for the instrument and the application to which the instrument is to be put. For example, this may improve the ability to manufacture tendon driven instruments which are interchangeable so that there is minimal variation in performance between the instruments being used.

In embodiments of the invention the method may comprise the further step of engaging each tensioning wire with a respective one of a plurality of primary pulleys substantially aligned with the plurality of ferrules, thereby tensioning each tendon to extend substantially coaxially with its respective ferrule.

In such embodiments of the invention each ferrule may be crimped to the respective tendon while the tendon is under tension and substantially coaxial with the ferrule. This avoids the tendon applying transverse forces to the ferrule during the crimping process which may damage the actuator that the ferrule forms part of, for example.

In embodiments of the invention the method comprises the further step of engaging each tensioning wire with a respective one of a plurality of secondary pulleys spaced apart from one another and wherein the step of hanging one of a plurality of predetermined weights from a second end of each tensioning wire comprises hanging each predetermined weight to hang below a respective secondary pulley.

In such embodiments of the invention the secondary pulleys may be spaced apart from one another such that the weights may hang spaced apart from one another. This may prevent the weights from resting on or supporting one another and ensure that each weight acts to tension the respective tendon as intended.

In embodiments of the invention the step of crimping each ferrule may comprise the steps of supporting each ferrule from a first direction and punching each ferrule from a second direction opposite to the first direction.

In such embodiments of the invention the plurality of ferrules may be supported from below and they may be punched from above. This means that the ferrules may be positioned in close proximity alongside one another as access is not required to the sides of each ferrule.

In embodiments of the invention the step of punching each ferrule may comprise the steps of punching each ferrule at a first location on the ferrule and punching each ferrule at a second location on the ferrule.

In such embodiments of the invention punching each ferrule in two locations to crimp it to the respective tendon may improve how securely the ferrule is attached to the tendon.

In embodiments of the invention the step of punching each ferrule at a first location may comprise punching each ferrule a first predetermined number of times at the first location on the ferrule and the step of punching each ferrule at a second location may comprise punching each ferrule a second predetermined number of times at the second location on the ferrule.

In such embodiments of the invention, the first and second predetermined number of times for punching the ferrule at the first and second locations respectively may be determined to ensure that each ferrule is securely attached to its respective ferrule. The more times that the ferrule is punched, the more secure the attachment may be. However, beyond a certain number of punches the improvement to the attachment may become negligible and the time required to carry out the further punches may be wasted.

The first and second predetermined numbers may be equal or may be different.

In embodiments of the invention the plurality of ferrules forms part of a drive module and the ferrules are movable relative to one another, and the method comprises the further step of immobilising the plurality of ferrules prior to resting each ferrule in its respective groove.

In such embodiments of the invention the drive module may comprise a plurality of actuators moveable linearly and parallel to one another, each actuator comprising a respective one of the ferrules. Immobilising the plurality of ferrules may improve the ease and repeatability with which the ferrules can be punched. Immobilising the plurality of ferrules may also improve the repeatability of crimping each ferrule to a particular position on the respective tendon while it is tensioned.

In embodiments of the invention the actuatable module is engageable with a housing configured to immobilise each ferrule when the actuatable module is engaged, and the step of immobilising the plurality of ferrules comprises engaging the actuatable module with a housing and locking the actuatable module in engagement with the housing.

In such embodiments of the invention the housing may be adapted to lock each actuator in a fixed position while the housing is engaged with the actuatable module, thereby immobilising the ferrules.

BRIEF DESCRIPTION OF THE DRAWINGS

Embodiments will now be described by way of example only with reference to the accompanying drawings in which.

DETAILED DESCRIPTION OF THE EMBODIMENTS

Figure 1:
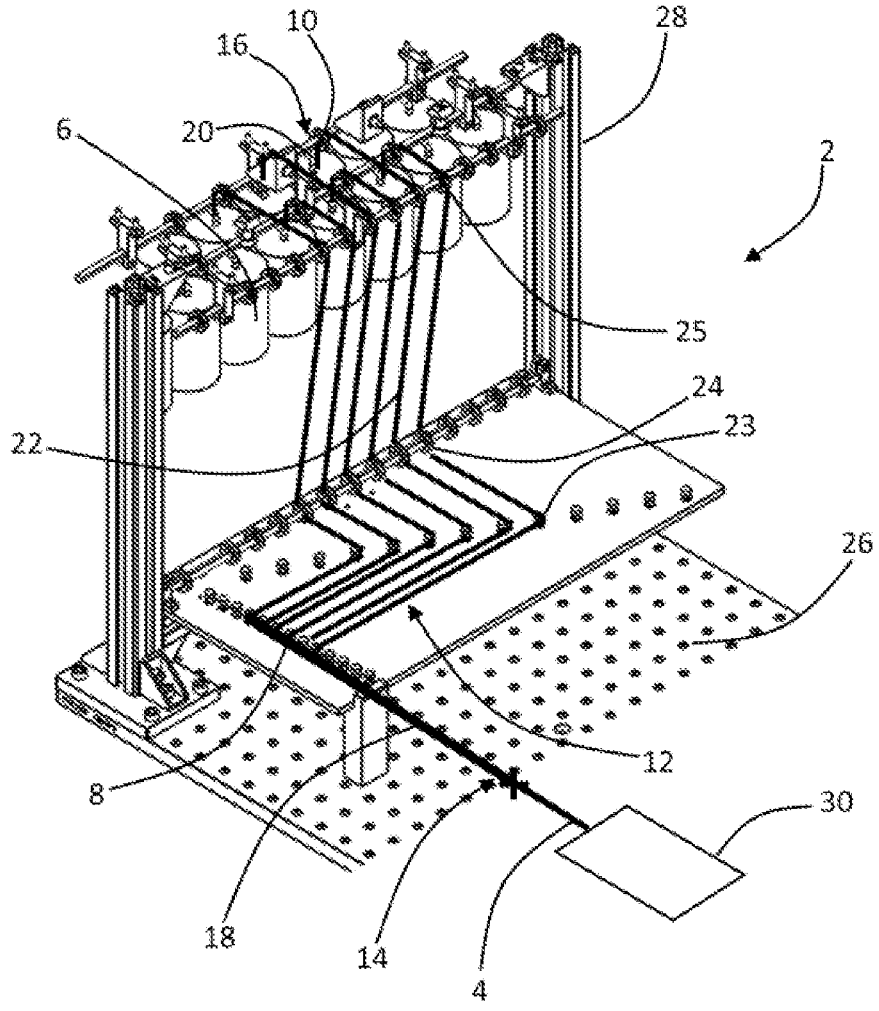
FIG. 1 is a schematic representation of a tensioning rig according to an embodiment of the first aspect of the invention.
Figure 2:
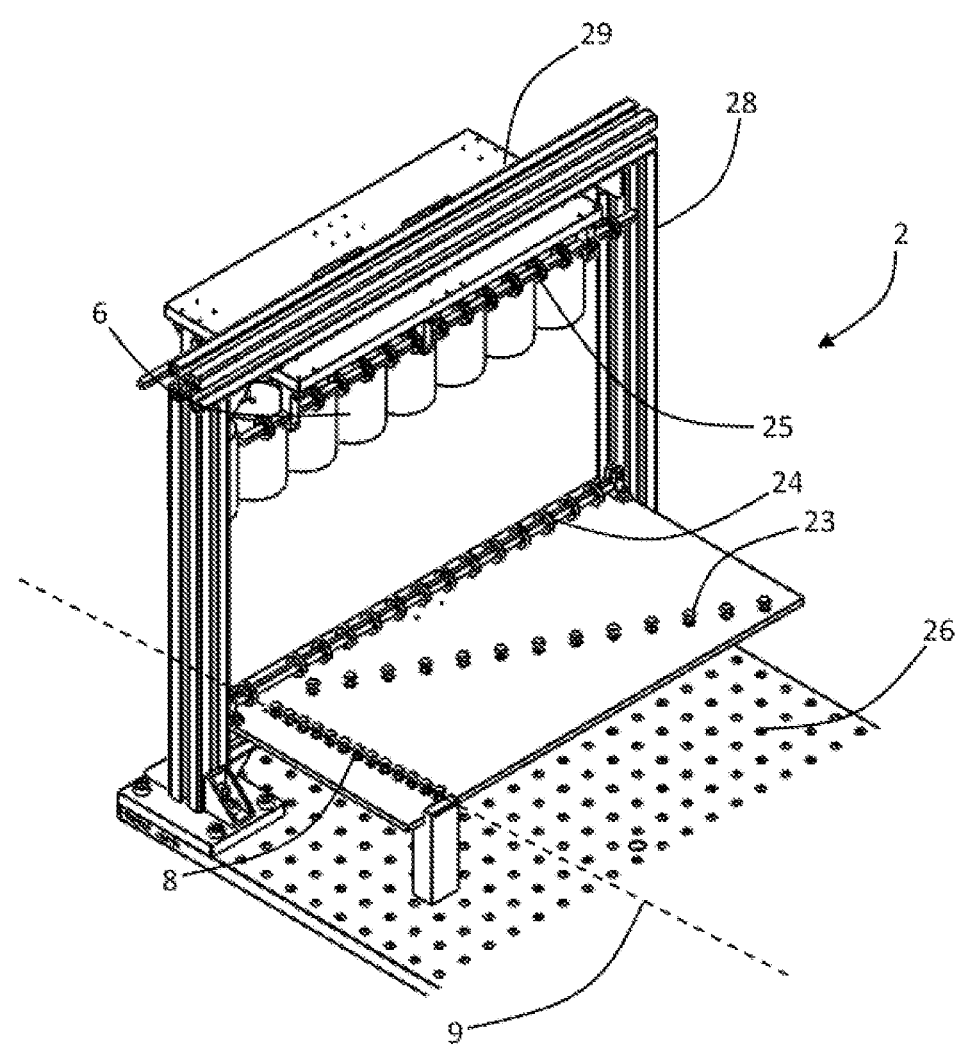
FIG. 2 is a schematic representation of the tensioning rig shown in FIG. 1 with a support beam shown.

Referring initially to FIGS. 1 and 2, a tensioning rig according to an embodiment of the first aspect of the invention is designated generally by the reference numeral 2. The tensioning rig 2 comprises a plurality of weights 6, a plurality of primary pulleys 8, a plurality of secondary pulleys 10, a base 26 and a support 28. The primary pulleys 8 are spaced apart from one another along a first axis 9 (shown in FIG. 2) and are supported by the base 26. The support 28 extends from the base 26 and is adapted to support the plurality of secondary pulleys 10 above the base 26 and spaced apart from one another. In FIG. 2 the support 28 is shown to comprise a support beam 29 which supports the plurality of secondary pulleys 10 whereas, in FIG. 1, the support beam 29 is omitted in order to reveal the secondary pulleys 10 and weights 6 positioned beneath the support beam 29.

The tensioning rig 2 also comprises a plurality of tensioning wires 12. Each tensioning wire 12 comprises a first end 14 comprising a tendon portion 18 and second end 16 comprising a weight portion 20. Each tendon portion 18 is attached to a respective tendon 4 while each weight portion 20 is attached to a respective weight 6. Further, each tensioning wire 12 is engaged with respective primary and secondary pulleys 8, 10. Each tendon portion 18 is extendable from the respective tendon 4 to the respective primary pulley 8 substantially along the first axis and each weight portion 20 is extendable from the respective secondary pulley 10 to the respective weight 6. Each tensioning wire 12 further comprises an intermediate portion 22 extendable from the respective primary pulley 8 to the respective secondary pulley 10.

In this embodiment of the invention the tensioning rig 2 further comprises a plurality of first auxiliary pulleys 23, a plurality of second auxiliary pulleys 24 and a plurality of third auxiliary pulleys 25. Each of the first, second and third auxiliary pulleys 23, 24, 25 is positioned between respective primary and secondary pulleys 8, 10. The intermediate portion 22 of each tensioning wire 12 is engaged with respective first, second and third auxiliary pulleys 23, 24, 25 as it extends between the respective primary and secondary pulleys 8, 10.

The tendons 4 form part of a tendon driven instrument 30. A first end of each tendon 4 is attached to the instrument 30 and a second end is attached to the respective tensioning wire 12. Therefore, when the tensioning rig 2 is in use as shown in FIG. 1, each tendon 4 and respective tensioning wire 12 extend between the instrument 30 and the weight 6. The weights 6 hang from the tensioning wires 12, below the secondary pulleys 10, and thereby tension both the tensioning wires 12 and the tendons 4. The degree of tension in each tendon is dependent on the mass of the respective weight 6.

The positioning of the plurality of primary pulleys 8 along the first axis 9 (shown in FIG. 2) allows each of the plurality of tendons 4 to be tensioned while extending substantially along the first axis 9. The plurality of first auxiliary pulleys 23 are positioned such that the plurality of tendons 4 are separated and spaced further apart in a direction substantially normal to the first axis. The plurality of second auxiliary pulleys 24 are adapted to direct the plurality of tendons 4 up towards the plurality of third auxiliary pulleys 25 and the plurality of secondary pulleys 10. The plurality of third auxiliary pulleys 25 are configured to direct the plurality of tendons 4 towards the secondary pulleys over the weights 6. The secondary pulleys are spaced apart in two rows where the pulleys in each row are off-set from one another to space them apart further without taking up excess space overall. The spacing of the secondary pulleys provides sufficient space for the plurality of weights 6 to hang below without interfering with one another.

Each tensioning wire 12 is removably attachable to the respective weight 6 to allow both the weights 6 and the tensioning wires 12 to be replaceable and interchangeable. The weight 6 hanging from each tensioning wire 12 may therefore be changed to vary the tension experienced by the associated tendon 4, for example a 100 g weight 6 may be swapped with a 200 g weight to increase tension exerted on the tendon 4. Also, the tensioning wires 12 may be replaced if they are damaged or worn, for example.

Figure 3:
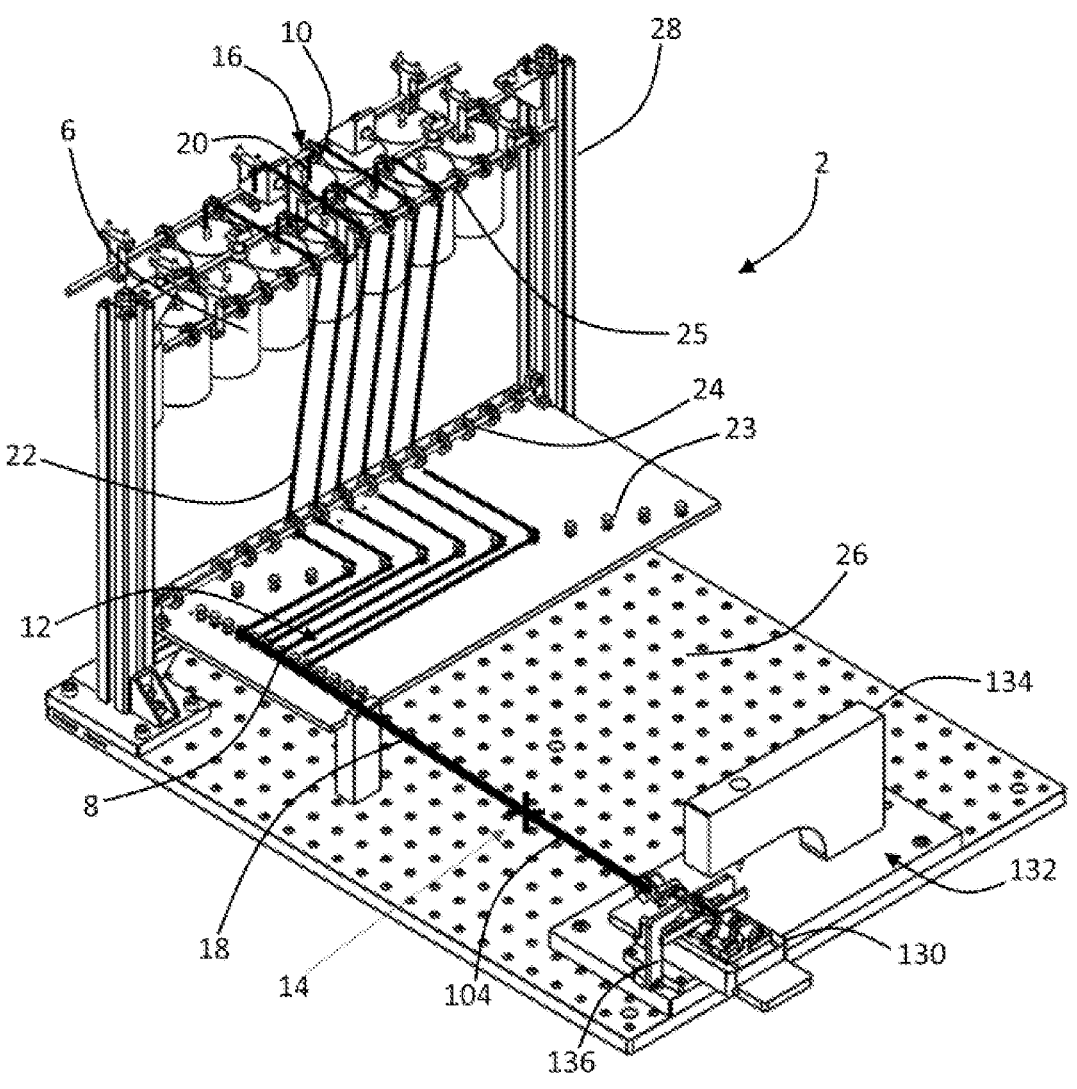
FIG. 3 is a schematic representation of the tensioning rig shown in FIG. 1 in use with a crimping rig.

Referring now to FIG. 3, the tensioning rig 2 is shown in use tensioning a plurality of tendons 104 that forms part of a tendon driven instrument 130. The tensioning rig 2 is in use with a crimping rig 132 comprising a punching rig 134 and a support bridge 136.

Figure 4:
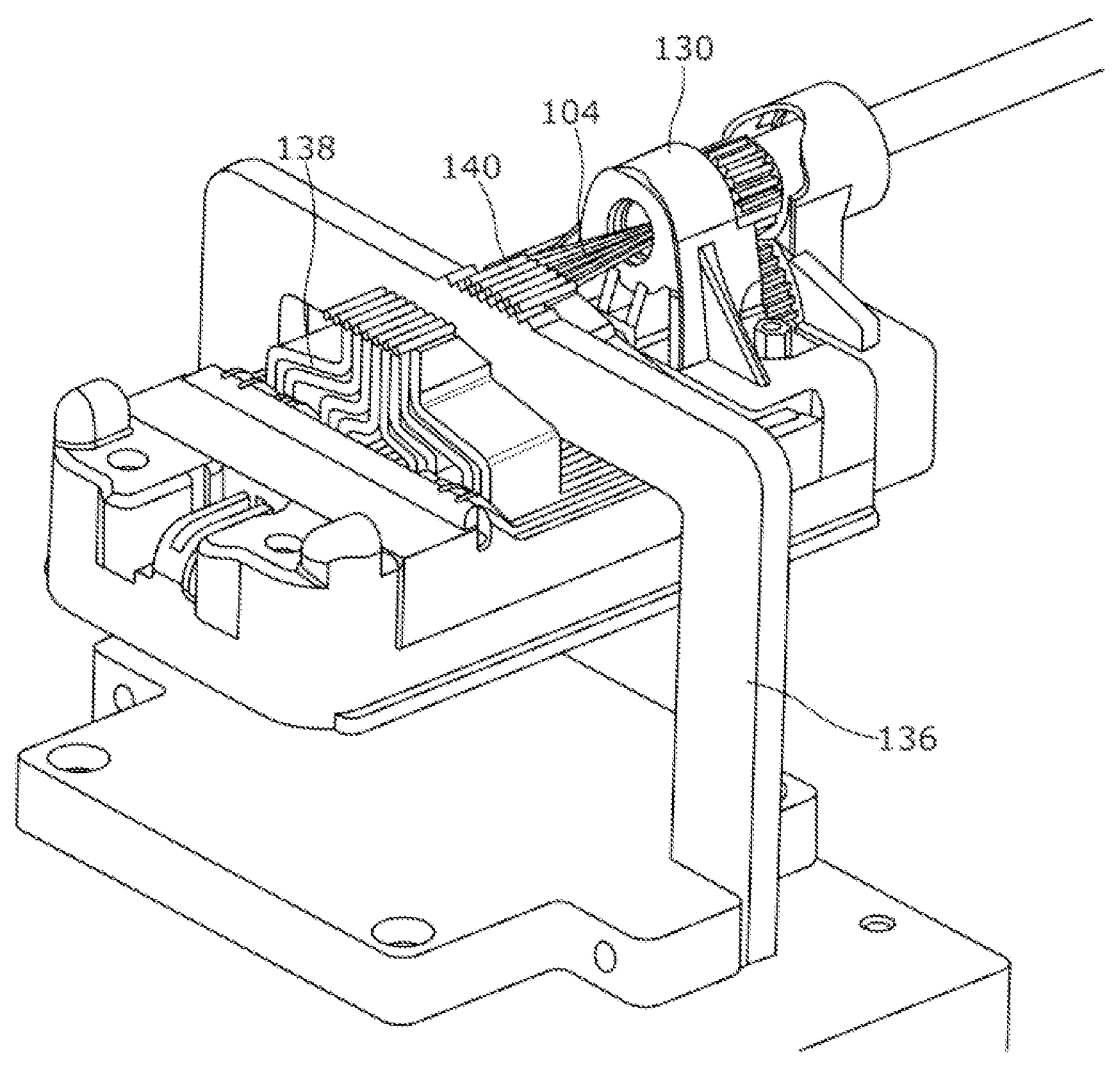
FIG. 4 is a schematic representation of a support bridge forming part of the crimping rig shown in FIG. 3.

Referring now to FIG. 4, the tendon driven instrument 130 comprises a plurality of actuators 138 moveable linearly and parallel to one another. Each actuator 138 comprises a ferrule 140 and the tendon driven instrument 130 is positioned such that a plurality of the ferrules rest on the support bridge 136. A respective plurality of tendons 104 are fixed to the tendon drive instrument at a first end and are threaded through each of the ferrules 140. From the ferrules 140, the tendons 104 may extend to the tensioning rig 2, as shown in FIG. 3, where they may be attached to a respective tensioning wire 12, and particularly to the tendon portion 18.

Referring back to FIG. 3, the punching rig 134 may be used to punch the ferrules 140 as they rest on the support bridge 136 and while the tendons 104 extend through them under tension provided by the tensioning rig 2. The ferrules 140 may therefore be crimped to the tendons 104.

Figure 5:
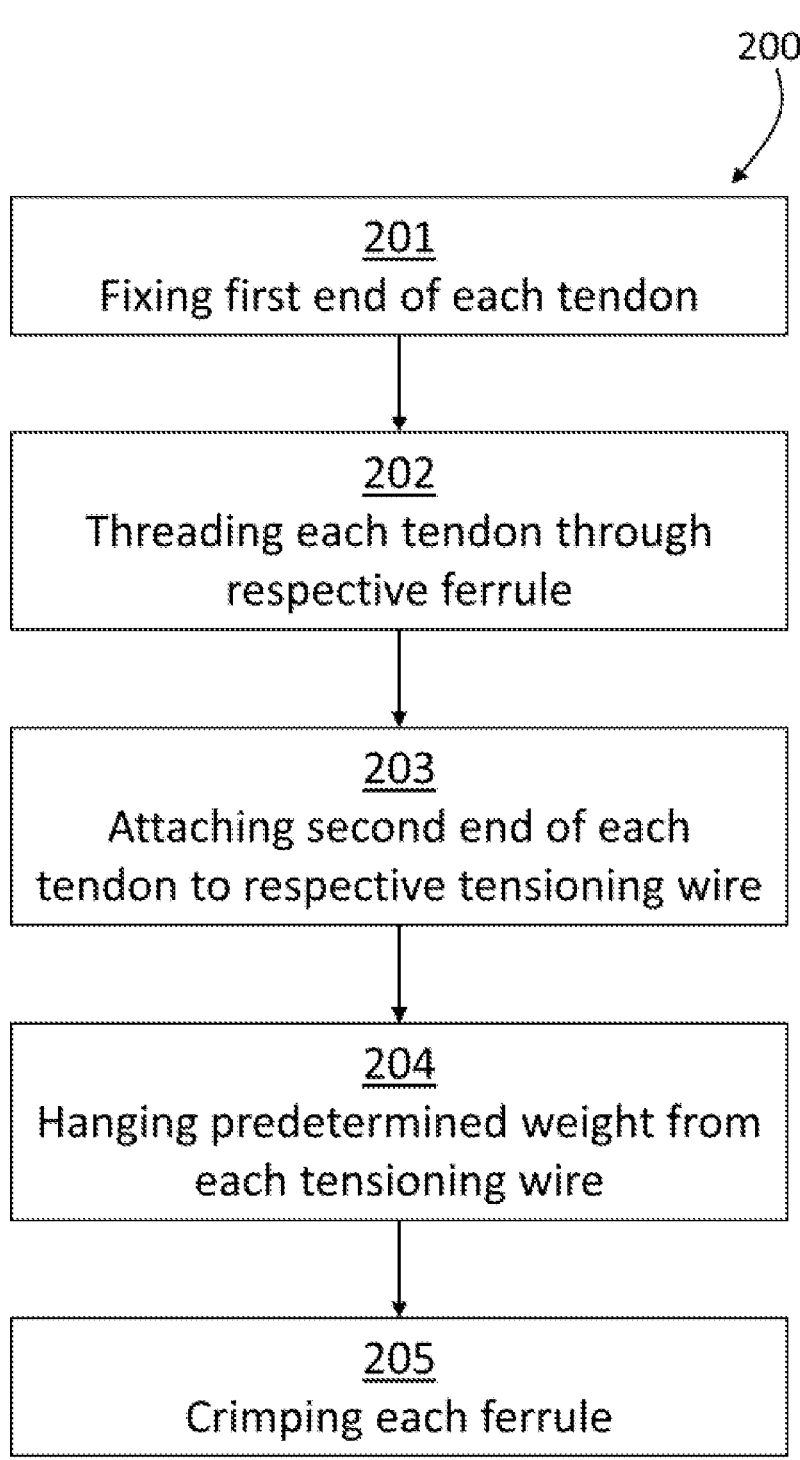
FIG. 5 is a schematic representation of a method according to the second aspect of the invention.

Referring now to FIG. 5, a method according to the second aspect of the invention of crimping a plurality of tendons within a plurality of ferrules, wherein each tendon comprises a first end and second end, is designated generally by the reference numeral 200. The method 200 comprises steps 201, 202, 203, 204 and 205 described below and may be performed using the tensioning rig 2 shown in FIGS. 1 to 3. Accordingly, steps 201 to 205 are described with reference to the features of FIGS. 3 and 4. However, it is to be understood that the method 200 may be carried out using any suitable apparatus.

Step 201

Fixing the first end of each tendon 104 such that it is immobilised relative to its respective ferrule 140.

Step 202

Threading each of the plurality of tendons 104 through a respective one of the plurality of ferrules 140.

Step 203

Attaching the second end of each tendon 104 to a first end of a respective one of a plurality of tensioning wires 12.

Step 204

Hanging one of a plurality of predetermined weights 6 from a second end of each tensioning wire 12.

The final step performed of steps 201 to 204 results in the plurality of tendons 104 being tensioned by the weights 6 via the tensioning wires 12. In the order provided above, the step of hanging one of a plurality of predetermined weights 6 from a second end of each tensioning wire 12 results in the tensioning of each tendon 104. However, steps 201 to 204 may be carried out in any order except an order in which step 202 is attempted as the final step. For example, the order of steps 201 to 204 may be reversed wherein the step of fixing the first end of each tendon 104 such that it is immobilised relative to its respective ferrule 140 results in the tensioning of each tendon 104.

Each tensioning wire 12 may be engaged with a respective primary pulley 8 substantially aligned with the plurality of ferrules 140, thereby tensioning each tendon 104 to extend substantially coaxially with its respective ferrule 140.

Each tensioning wire 12 may also be engaged with a respective one of a plurality of secondary pulleys 10 spaced apart from one another. Accordingly, step 204 may comprise hanging each predetermined weight 6 to hang below a respective secondary pulley 10. The secondary pulleys 10 may be spaced apart from one another such that the weights 6 may hang spaced apart from one another. This may prevent the weights 6 from resting on or supporting one another and ensure that each weight 6 acts to tension the respective tendon 104 as intended.

Step 205

Crimping each ferrule 140 to its respective tendon 104.

Each ferrule 140 may be crimped to the respective tendon 104 while the tendon 104 is under tension and substantially coaxial with the ferrule 140 by virtue of each tensioning wire 12 being engaged with a respective primary pulley 8. This avoids the tendon 104 applying transverse forces to the ferrule 140 during the crimping process which may damage the actuator 138, for example.

Step 205 may comprise the steps of supporting each ferrule 140 from a first direction and punching each ferrule 140 from a second direction opposite to the first direction. For example, the support bridge 136 shown in FIGS. 3 and 4 may be used to support the ferrules 140 from below while the punching rig 134 may be used to punch each ferrule 140 from above. Other suitable apparatus may also be used. An advantage of this method is that the ferrules 140 may be crimped despite being positioned very close together, as shown in FIG. 4. This contrasts against known crimping methods which require the use of crimping tools that cannot operate with such confined access to the ferrules.

The step of punching each ferrule 140 may comprise the steps of punching each ferrule 140 at a first location on the ferrule 140 and punching each ferrule 140 at a second location on the ferrule 140. Punching each ferrule 140 in two locations to crimp it to the respective tendon 104 may improve how securely the ferrule 140 is attached to the tendon 104.

Further, each ferrule 140 may be punched in each location a predetermined number of times determined to ensure that each ferrule 140 is securely attached to its respective tendon 104.

Preferences and options for a given aspect, feature or parameter of the invention should, unless the context indicates otherwise, be regarded as having been disclosed in combination with any and all preferences and options for all other aspects, features and parameters of the invention. For example, the first aspect of the invention should be regarded as having been disclosed comprising any number of auxiliary pulleys, i.e., more than, fewer than or the same number as the number of auxiliary pulleys shown in FIGS. 1 to 3.

The invention claimed is:

1. A method of attaching a plurality of tendons to a corresponding plurality of tensioning wires using a plurality of corresponding ferrules, the method comprising the steps of:

providing a support bridge with a plurality of grooves formed thereon;

immobilising the ferrules;

once immobilised, resting the ferrules in the grooves;

fixing each tendon such that it is immobilised relative to its a respective ferrule, threading each of the plurality of tendons into the respective ferrule, aligning each tendon to a first end of a respective one of a plurality of tensioning wires, hanging one of a plurality of predetermined weights from a second end of each tensioning wire, and crimping each ferrule to its respective tendon.

2. A method according to claim 1 comprising the further step of engaging each tensioning wire with a respective one of a plurality of primary pulleys substantially aligned with the plurality of ferrules, thereby tensioning each tendon to extend substantially coaxially with its respective ferrule.

3. A method according to claim 2 comprising the further step of engaging each tensioning wire with a respective one of a plurality of secondary pulleys spaced apart from one another and wherein the step of hanging one of a plurality of predetermined weights from a second end of each tensioning wire comprises hanging each predetermined weight to hang below a respective secondary pulley.

4. A method according to claim 1, wherein the step of crimping each ferrule comprises the steps of supporting each ferrule from a first direction and punching each ferrule from a second direction opposite to the first direction.

5. A method according to claim 4, wherein the step of punching each ferrule comprises the steps of punching each ferrule at a first location on the ferrule and punching each ferrule at a second location on the ferrule.

6. A method according to claim 5 wherein the step of punching each ferrule at a first location comprises punching each ferrule a first predetermined number of times at the first location on the ferrule.

7. A method according to claim 6, wherein the step of punching each ferrule at a second location comprises punching each ferrule a second predetermined number of times at the second location on the ferrule.

8. A method according to claim 1, wherein the ferrules form part of a drive module and the ferrules are movable relative to one another as part of the drive module.

9. A method according to claim 8, wherein an actuatable module is engageable with a housing configured to immobilise each ferrule when the actuatable module is engaged, and the step of immobilising the ferrules comprises engaging the actuatable module with a housing and locking the actuatable module in engagement with the housing.

* * * * *